United States Patent
Chassot et al.

(10) Patent No.: US 6,699,990 B2
(45) Date of Patent: Mar. 2, 2004

(54) 3-(2,5-DIAMINOPHENYL)-ACRYLAMIDE DERIVATIVES AND COLORING AGENTS CONTAINING SAID COMPOUNDS

(75) Inventors: Laurent Chassot, Praroman (CH); Hans-Juergen Braun, Ueberstorf (CH)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 10/258,320

(22) PCT Filed: Oct. 18, 2001

(86) PCT No.: PCT/EP01/12054

§ 371 (c)(1), (2), (4) Date: Oct. 21, 2002

(87) PCT Pub. No.: WO02/074731

PCT Pub. Date: Sep. 26, 2002

(65) Prior Publication Data

US 2003/0140431 A1 Jul. 31, 2003

(30) Foreign Application Priority Data

Mar. 17, 2001 (DE) .......................... 101 13 027

(51) Int. Cl.[7] .................. A61K 7/13; C07C 233/11; C07D 295/192
(52) U.S. Cl. .................. 544/165; 8/409; 8/410; 8/408; 546/221; 546/300; 546/307; 546/308; 546/309; 548/338.1; 548/372; 548/537; 548/540; 548/550; 549/439; 549/493; 560/312; 562/450; 564/163
(58) Field of Search .................. 544/165; 546/307, 546/309; 549/493; 564/163; 8/408

(56) References Cited

FOREIGN PATENT DOCUMENTS

| DE | 39 17 304 A1 | 11/1990 |
| DE | 198 22 041 A1 | 12/1999 |
| EP | 0 007 537 A | 2/1980 |
| EP | 0 634 163 A1 | 1/1995 |
| EP | 0 797 980 A | 10/1997 |
| EP | 0 819 424 A1 | 1/1998 |
| WO | 99 59527 A | 11/1999 |

OTHER PUBLICATIONS

Organic Synthesis, Kapitel 7, "Protection for the Amino Group", pp. 309–404, Wiley Interscience 1991.

Primary Examiner—Robert W. Ramsuer
(74) Attorney, Agent, or Firm—Michael J. Striker

(57) ABSTRACT

The present patent application relates to 3-(2,5-diaminophenyl)acrylamide derivatives of general formula (I) or to physiologically tolerated, water-soluble-salts thereof

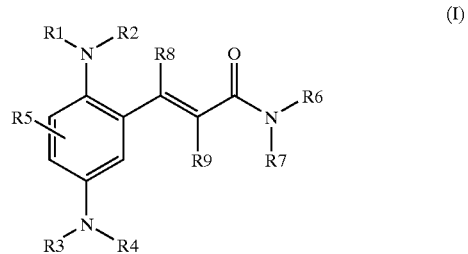

and to agents containing said compounds and used for oxidative dyeing of fibers.

11 Claims, No Drawings

3-(2,5-DIAMINOPHENYL)-ACRYLAMIDE DERIVATIVES AND COLORING AGENTS CONTAINING SAID COMPOUNDS

BACKGROUND OF THE INVENTION

The invention relates to novel 3-(2,5-diaminophenyl) acrylamide derivatives and to dyeing agents for keratin fibers containing these compounds.

In the area of keratin fiber dyeing, particularly hair dyeing, oxidation dyes have attained substantial importance. In this case, the coloration is produced by reaction of certain developers with certain couplers in the presence of an appropriate oxidant. Suitable developers are, in particular, 2,5-diaminotoluene, 2,5-diaminophenylethyl alcohol, p-aminophenol, 1,4-diaminobenzene and 4,5-diamino-1-(2-hydroxyethyl)pyrazole, and suitable couplers are, for example, resorcinol, 2-methylresorcinol, 1-naphthol, 3-aminophenol, m-phenylenediamine, 2-amino-4-(2'-hydroxyethyl)aminoanisole, 1,3-diamino-4-(2'-hydroxyethoxy)benzene and 2,4-diamino-5-fluorotoluene.

To cover the important blond range, direct aromatic nitro dyes, in particular, were heretofore added to the oxidative hair colorants.

The use of substituted p-phenylenediamines as dye components in oxidative hair colorants is known from the literature, for example from German Unexamined Patent Application DE 198 22 041, Unexamined European Patent Applications EP 0 634 163 and EP 0 819 424, German Unexamined Patent Application 39 17 304 and European Unexamined Patent Application 0 007 537. These compounds, however, do not meet the requirements placed on dyes for oxidative colorants for the blond range in all respects. Hence, the need for suitable novel dyes continued to exist.

SUMMARY OF THE INVENTION

We have now found; that certain p-phenylenediamine derivatives together with the usual couplers make it possible to achieve an intense blond coloration of fibers, particularly keratin fibers, for example hair. By use of these p-phenylenediamine derivatives in an oxidizing medium, intense color shades are thus obtained which are unusually light-fast and wash-fast.

Hence, the object of the present invention are 3-(2,5-diaminophenyl)acrylamide derivatives of general formula (I) or their physiologically tolerated, water-soluble salts

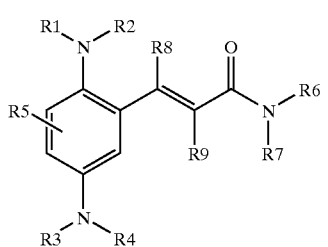

wherein

R1, R2, R3 and R4 can be equal or different and independently of each other denote hydrogen, a $C_1$–$C_6$-alkyl group, a $C_2$–$C_4$-hydroxyalkyl group or a $C_3$–$C_4$-dihydroxyalkyl group or R1 and R2 or R3 and R4 form a four-membered to eight-membered aliphatic ring and at least two of the R1 to R4 groups denote hydrogen;

R5 denotes hydrogen, a halogen atom (F, Cl, Br, I), a $C_1$–$C_4$-alkyl group, a $C_1$–$C_4$-hydroxyalkyl group or a $C_1$–$C_4$-alkoxy group;

R6 and R7 can be equal or different and independently of each other denote hydrogen, a $C_1$–$C_2$-alkoxy, $C_1$–$C_6$-alkyl, unsaturated $C_3$–$C_6$-alkyl, $C_2$–$C_4$-hydroxyalkyl, $C_3$–$C_4$-dihydroxyalkyl, $C_2$–$C_4$-aminoalkyl, $C_2$–$C_4$-dimethylaminoalkyl, $C_2$–$C_4$-acetylaminoalkyl, $C_2$–$C_4$-methoxyalkyl, $C_2$–$C_4$-ethoxyalkyl, $C_1$–$C_4$-cyanoalkyl, $C_1$–$C_4$-carboxyalkyl, $C_2$–$C_4$-aminocarbonylalkyl group, a pyridylmethyl, furfuryl, hydrogenated furfuryl, substituted pyridyl group, a group of formula (II)

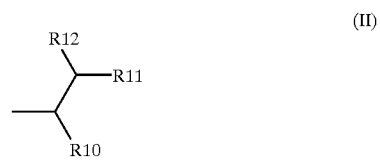

a group of formula (III)

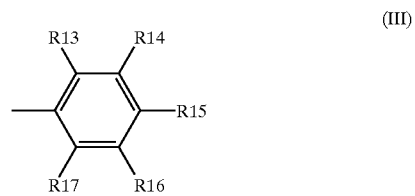

or a group of formula (IV)

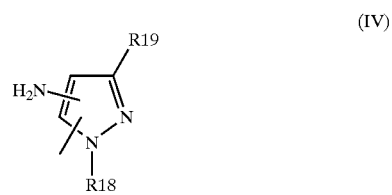

or R6 and R7 form a ring of formula

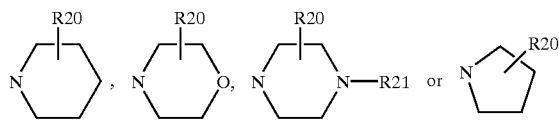

R8, R9 and R21 can be equal or different and independently of each other denote hydrogen or a $C_1$–$C_6$-alkyl group;

R10 denotes hydrogen, a carboxy group or an aminocarbonyl group;

R11 and R12 can be equal or different and independently of each other denote hydrogen, a hydroxyl, aminocarbonyl, methylthiomethyl group, a phenyl- or hydroxyl-substituted phenyl group or a group of formula

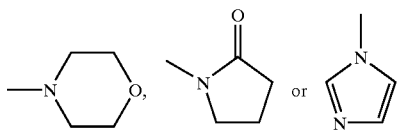

R13, R14, R15, R16 and R17 can be equal or different and independently of each other denote hydrogen. a halogen atom (F, Cl, Br, I), a cyano group, a hydroxyl, $C_1$–$C_4$-alkoxy, $C_1$–$C_4$-hydroxyalkoxy, $C_1$–$C_6$-alkyl, $C_1$–$C_4$-alkyl thioether, mercapto, nitro, amino, alkylamino, hydroxyalkylamino, dialkylamino, di(hydroxyalkyl)amino, (dihydroxyalkyl)amino, (hydroxyalkyl)alkylamino, trifluoromethane, —C(O)H, —C(O)CH$_3$, —C(O)CF$_3$, —Si(CH$_3$)$_3$, $C_1$–$C_4$-hydroxyalkyl or $C_2$–$C_4$-dihydroxyalkyl group or two adjacent R13 to R17 groups together form an —O—CH$_2$—O— bridge;

R18 denotes a $C_1$–$C_4$-alkyl, benzyl or $C_1$–$C_4$-hydroxyalkyl group;

R19 denotes hydrogen or a $C_1$–$C_6$-alkyl group, and

R20 denotes hydrogen, a hydroxyl, carboxy, aminocarbonyl or hydroxymethyl group.

Noteworthy among compounds of formula (I) are, for example:

3-(2,5-diaminophenyl)-N-methylacrylamide, 3-(2,5-diaminophenyl)-N-propylacrylamide, 3-(2,5-diaminophenyl)-1-morpholin-4-ylpropenone, 3-(2,5-diaminophenyl)-N-(1-hydroxymethylpropyl)acrylamide, 3-(2,5-diaminophenyl)-N-furan-2-ylmethylacrylamide, 3-(2,5-diaminophenyl)-N-methoxy-N-methylacrylamide, 3-(2,5-diaminophenyl)-N-(2-hydroxy-1-methylethyl)acrylamide, N-(2-aminoethyl)-3-(2,5-diaminophenyl)acrylamide, 3-(2,5-diaminophenyl)-N-(tetrahydrofuran-2-ylmethyl)acrylamide, N-cyclopropyl-3-(2,5-diaminophenyl)acrylamide, 3-(2,5-diaminophenyl)-N-isopropylacrylamide, 3-(2,5-diaminophenyl)-N-(2-methoxyethyl)acrylamide, 3-(2,5-diaminophenyl)-1-(4-hydroxypiperidin-1-yl)propenone, N-(2-acetylaminoethyl)-3-(2,5-diaminophenyl)acrylamide, 3-(2,5-diaminophenyl)-N-(2-morpholin-4-ylethyl)acrylamide, 3-(2,5-diaminophenyl)-N-[3-(2-ketopyrrolidin-1-yl)propyl]acrylamide, 2-[3-(2,5-diaminophenyl)acryloylamino]-3-methylbutyric acid, [3-(2,5-diaminophenyl)acryloylamino]acetic acid, N-allyl-3-(2,5-diaminophenyl)acrylamide, 3-(2,5-diaminophenyl)-N-[2-(5-nitropyridin-2-ylamino)ethyl]acrylamide, 3-(2,5-diaminophenyl)-N-(3-imidazol-1-ylpropyl)acrylamide, 3-(2,5-diaminophenyl)-N-[2-(3H-imidazol-4-yl)ethyl]acrylamide, N-(4-aminophenyl)-3-(2,5-diaminophenyl)acrylamide, 3-(2,5-diaminophenyl)-N-[2-(4-sulfamoylphenyl)ethyl]acrylamide, N-[5-chloro-4-(2-hydroxyethylamino)-2-nitrophenyl]-3-(2,5-diaminophenyl)acrylamide, 3-(2,5-diaminophenyl)-1-pyrrolidin-1-ylpropenone, 3-(2,5-diaminophenyl)-N-pyridin-2-ylacrylamide, N-[3-(2,5-diaminophenyl)-2-propenoyl]-L-glutamic acid trifluoroacetate, N2-[3-(2,5-diaminophenyl)-2-propenoyl]-glutamine trifluoroacetate, N-[4-amino-2-(2-hydroxyethyl)-2H-pyrazol-3-yl]-3-(2,5-diaminophenyl)acrylamide, N-(4-amino-2(3)-methylphenyl)-3-(2,5-diaminophenyl)acrylamide, N-[4-amino-2(3)-(2-hydroxyethyl)phenyl]-3-(2,5-diaminophenyl)acrylamide, N-{4-[bis-(2-hydroxyethyl)amino]phenyl}-3-(2,5-diaminophenyl)acrylamide, 3-(2,5-diaminophenyl)-N-(4-hydroxyphenyl)acrylamide, 3-(2,5-diaminophenyl)-N-(3-hydroxy-4-methylphenyl)acrylamide, N-(3-aminophenyl)-3-(2,5-diaminophenyl)acrylamide, 3-(2,5-diaminophenyl)-N-(3-hydroxy-5-hydroxymethyl-2-methyl-4-pyridinylmethyl)acrylamide, 3-(2,5-diaminophenyl)-N-(2-hydroxy-5-nitrophenyl)acrylamide, N-(3-chloro-2-hydroxy-5-nitrophenyl)-3-(2,5-diaminophenyl)acrylamide, 3-(2,5-diaminophenyl)-1-(2-hydroxymethyl-1-pyrrolidinyl)propenone, 3-(2,5-diaminophenyl-1-(3-hydroxy-1-pyrrolidinyl)propenone, 1-[3-(2,5-diaminophenyl)acryloyl]pyrrolidine-2-carboxamide, 3-(2,5-diaminophenyl)-1-(3-hydroxy-1-piperidinyl)propenone, 3-(2,5-diaminophenyl)-N-(2-hydroxy-1-hydroxymethylethyl)acrylamide, N-(1-carbamoyl-2-hydroxyethyl)-3-(2,5-diaminophenyl)acrylamide, N-[3-(2,5-diaminophenyl)-2-propenoyl]-L-aspartic acid, N2-[3-(2,5-diaminophenyl)-2-propenoyl]-L-asparagine, N-[3-(2,5-diaminophenyl)-2-propenoyl]-L-leucine, N-[5-amino-2(4)-2-hydroxyethoxy)phenyl]-3-(2,5-diaminophenyl)acrylamide, 3-(2,5-diaminophenyl)-N-ethylacrylamide, N-benzo[1,3]dioxol-5-yl-3-(2,5-diaminophenyl)acrylamide, 2-[3-(2,5-diaminophenyl)acryloylamino]-4-methylpentanoic acid, 3-(2,5-diaminophenyl)-1-(6,7-dihydroxy-1-methyl-3,4-dihydro-1H-isoquinolin-2-yl)propenone, N-(4-aminophenyl)-3-($N^2$,$N^2$-bis-methyl-2,5-diaminophenyl)acrylamide, N-(4-aminophenyl)-3-($N^5$,$N^5$-bis-methyl-2,5-diaminophenyl)acrylamide, N-(4-aminophenyl)-3-[$N^2$,$N^2$-bis-(2-hydroxyethyl)-2,5-diaminophenyl]acrylamide, N-(4-aminophenyl)-3-[$N^5$,$N^5$-bis-(2-hydroxyethyl)-2,5-diaminophenyl]acrylamide, N-(4-aminophenyl)-3-[$N^2$-(2,3-dihydroxypropyl)-2,5-diaminophenyl]acrylamide, N-(4-aminophenyl)-3-[$N^5$-(2,3-dihydroxypropyl)-2,5-diaminophenyl]acrylamide, N-(4-aminophenyl)-3-[2-(1-pyrrolidinyl)-5-aminophenyl]acrylamide, N-(4-aminophenyl)-3-[5-(1-pyrrolidinyl)-2-aminophenyl]acrylamide, 3-$N^2$,$N^2$-bis-methyl-2,5-diaminophenyl-N-ethylacrylamide, 3-[$N^5$,$N^5$-bis-methyl-2,5-diaminophenyl]-N-ethylacrylamide, 3-[$N^2$,$N^2$-bis-(2-hydroxyethyl)-2,5-diaminophenyl]-N-ethylacrylamide, 3-[$N^5$,$N^5$-bis-(2-hydroxyethyl)-2,5-diaminophenyl]-N-ethylacrylamide, 3-[$N^2$-(2,3-dihydroxypropyl)-2,5-diaminophenyl]-N-ethylacrylamide, 3-[$N^5$-(2,3-dihydroxypropyl)-2,5-diaminophenyl]-N-ethylacrylamide, 3-[2-(1-pyrrolidinyl)-5-aminophenyl]-N-ethylacrylamide, 3-[5-(1-pyrrolidinyl)-2-aminophenyl]-N-ethylacrylamide, 3-($N^2$,$N^2$-bis-methyl-2,5-diaminophenyl)-N-propylacrylamide, 3-($N^5$,$N^5$-bis-methyl-2,5-diaminophenyl)-N-propylacrylamide, 3-[$N^2$,$N^2$-bis-(2-hydroxyethyl)-2,5-diaminophenyl]-N-propylacrylamide, 3-[$N^5$,$N^5$-bis-(2-hydroxyethyl)-2,5-diaminophenyl]-N-propylacrylamide, 3-[$N^2$-(2,3-dihydroxypropyl)-2,5-diaminophenyl]-N-propylacrylamide, 3-[$N^5$-(2,3-dihydroxypropyl)-2,5-diaminophenyl]-N-propylacrylamide, 3-[2-(1-pyrrolidinyl)-5-aminophenyl]-N-propylacrylamide, 3-[5-(1-pyrrolidinyl)-2-aminophenyl]-N-propylacrylamide, 3-($N^2$,$N^2$-bis-methyl-2,5-diaminophenyl)-N-(2-hydroxy-1-methylethyl)acrylamide, 3-($N^5$,$N^5$-bis-methyl-2,5-diaminophenyl)-N-(2-hydroxy-1-methylethyl)acrylamide, 3-[$N^2$,$N^2$-bis-(2-hydroxyethyl)-2,5-diaminophenyl]-N-(2-hydroxy-1-methylethyl)acrylamide, 3-[$N^5$,$N^5$-bis-(2-hydroxyethyl)-2,5-diaminophenyl]-N-(2-hydroxy-1-methylethyl)acrylamide, 3-[$N^2$-(2,3-dihydroxypropyl)-2,5-diaminophenyl]-N-(2-hydroxy-1-methylethyl)acrylamide, 3-[$N^5$-(2,3-dihydroxypropyl)-2,5-diaminophenyl]-N-(2-hydroxy-1-methylethyl)acrylamide, 3-[2-(1-pyrrolidinyl)-5-aminophenyl]-N-(2-hydroxy-1-methylethyl)acrylamide, 3-[5-(1-pyrrolidinyl)-2-aminophenyl]-N-(2-hydroxy-1-methylethyl)acrylamide or the physiologically tolerated salts thereof.

Preferred compounds of formula (I) are those wherein (i) one or more of the R5, R8 and R9 groups denote hydrogen and/or (ii) R1, R2, R3 and R4 denote hydrogen and/or (iii) R6 denotes a methyl group, a methoxy group or a $C_2$–$C_4$ hydroxyalkyl group and R7 denotes a $C_2$–$C_4$-hydroxyalkyl group and/or (iv) R6 denotes hydrogen and R7 denotes a $C_1$–$C_6$-alkyl group, an unsaturated $C_3$–$C_6$-alkyl group, a $C_2$–$C_4$-hydroxyalkyl group, a furfuryl group, a substituted phenyl group or a substituted pyrazoyl group, and/or (v) R6 and R7 form an aliphatic ring of formula

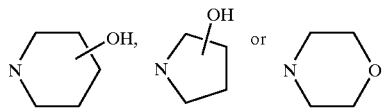

In particular, the following compounds are noteworthy:
3-(2,5-diaminophenyl)-N-propylacrylamide, 3-(2,5-diaminophenyl)-N-2-furanylmethylacrylamide, 3-(2,5-diaminophenyl)-N-methoxy-N-methylacrylamide, 3-(2,5-diaminophenyl)-N-(2-hydroxy-1-methylethyl)acrylamide, N-cyclopropyl-3-(2,5-diaminophenyl)acrylamide, 3-(2,5-diaminophenyl)-N-isopropylacrylamide, N-(4-aminophenyl)-3-(2,5-diaminophenyl)acrylamide, 3-(2,5-diaminophenyl)-1-pyrrolidin-1-ylpropenone, N-[4-amino-2-(2-hydroxyethyl)-2H-pyrazol-3-yl]-3-(2,5-diaminophenyl)acrylamide, N-(4-amino-2(3)-methylphenyl)-3-(2,5-diaminophenyl)acrylamide, N-{4-[bis-(2-hydroxyethyl)amino]phenyl}-3-(2,5-diaminophenyl)acrylamide, 3-(2,5-diaminophenyl)-N-(4-hydroxyphenyl)acrylamide, 3-(2,5-diaminophenyl)-1-(3-hydroxypyrrolidin-1-yl)propenone, N-[5-amino-2(4)-2-(hydroxyethoxy)phenyl]-3-(2,5-diaminophenyl)acrylamide and 3-(2,5-diaminophenyl)-N-ethylacrylamide.

The 3-(2,5-diaminophenyl)acrylamide derivatives of formula (I) can be used as the free bases as well as in the form of their physiologically tolerated salts with inorganic or organic acids, for example hydrochloric acid, sulfuric acid, phosphoric acid, acetic acid, propionic acid, lactic acid or citric acid.

The 3-(2,5-diaminophenyl)acrylamide derivatives of formula (I) of the invention can be prepared by known methods of synthesis. For example, the synthesis of the compound of the invention can be carried out as follows:

By aminolysis of a substituted benzene of formula (Ia)

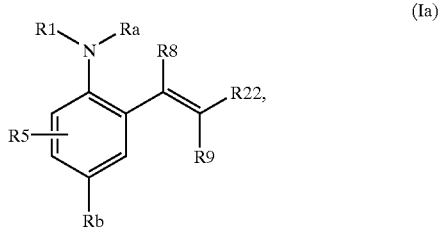

(Ia)

wherein Ra denotes an appropriate protective group, for example a group as described in Organic Synthesis, Chapter 7, "Protection for the Amino Group", page 309 ff, Wiley Interscience, 1991; Rb stands for NR1Ra or NR3R4 and R22 denotes a carboxylic acid group, a carboxylic acid chloride group, a carboxylate ester group of a carboxylic anhydride group,
  with an amine having formula NHR6R7,
    wherein R1, R3, R4, R5, R6, R7, R8 and R9 have the same meaning as in formula (I), followed by elimination of the protective group.

The 3-(2,5-diaminophenyl)acrylamide derivatives of formula (I) of the invention are readily water-soluble and give colorations of high intensity and excellent color stability, particularly in terms of light fastness, wash fastness and rubbing fastness.

Another object of the present invention are therefore agents for oxidative dyeing of keratin fibers, for example hair, furs, feathers or wool, particularly human hair, said agents being based on a developer-coupler combination which as developer contains at least one 3-(2,5-diaminophenyl)acrylamide derivative of formula (I).

The 3-(2,5-diaminophenyl)acrylamide derivative of formula (I) is contained in the colorant of the invention in an amount from about 0.005 to 20 wt. %, an amount from about 0.01 to 5 wt. % and particularly from 0.1 to 2.5 wt. % being preferred.

Preferred coupler compounds are N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethylamino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diamino-benzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diamino-phenoxyacetic acid, 3-[di(2-hydroxyethyl)amino]-aniline, 4-amino-2-di[(2-hydroxyethyl)amino]-1-ethoxybenzene, 5-methyl-2-(1-methylethyl)phenol, 3-[(2-hydroxy-ethyl)amino]-aniline, 3-[(2-aminoethyl)amino]aniline, 1,3-di(2,4-diaminophenoxy)-propane, di(2,4-diaminophenoxy)methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methyl-phenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methyl-phenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxy-ethyl)amino]phenol, 3-[(2-methoxyethyl)amino]-phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxy-ethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxy-benzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4[2H]benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolinedione, 1,3-diamino-4-(hydroxypropoxy)benzene, 1,3-diamino-4-(2-methoxyethoxy)benzene and 2,6-dihydroxy-3,4-dimethylpyridine.

Although the advantageous properties of the 3-(2,5-diaminophenyl)acrylamide derivatives of formula (I) described herein suggest that they should be used as the only developers, the 3-(2,5-diaminophenyl)acrylamide derivatives of formula (I) can, of course, also be used together with known developers, for example 1,4-diaminobenzene, 2,5-diaminotoluene, 1-(2,5-diaminophenyl)ethanol, 2-(2,5-diaminophenyl)ethanol, 4-aminophenol and derivatives thereof, for example 4-amino-3-methylphenol, 4,5-diaminopyrazole derivatives, for example 4,5-diamino-1-(2-hydroxyethyl)pyrazole, 4,5-diamino-1-benzylpyrazole and 4,5-diamino-1-(4-methylbenzylpyrazole, or tetraaminopyrimidines.

The couplers and developers can be present in the colorant of the invention either individually or in admixture with one another, the total amount of each of the couplers and developers in the colorant of the invention being about 0.005 to 20 wt. % preferably about 0.01 to 5 wt. % and particularly 0.1 to 2.5 wt. % (based on the total amount of colorant).

The total amount of the developer-coupler combination contained in the colorant described herein is preferably about 0.01 to 20 wt. %, an amount of about 0.02 to 10 wt. % and particularly 0.2 to 6 wt. % being particularly preferred. In general, the developers and couplers are used in approximately equimolar amounts, but it is not disadvantageous if the developer is present in a certain excess or deficiency.

Moreover, the colorant of the invention can additionally contain other dye components, for example 6-amino-2-methylphenol and 2-amino-5-methylphenol, as well as common direct dyes, for example triphenylmethane dyes such as 4-[(4'-aminophenyl)-(4'-imino-2",5"-cyclohexadien-1"-ylidene)methyl]-2-methylaminobenzene monohydrochloride (Color Index [C.I.] 42 510) and 4-[(4'-amino-3'-methylphenyl)-(4"-imino-3"-methyl-2",5"-cyclohexadien-1"-ylidene)methyl]-2-methylaminobenzene monohydrochloride (C.I. 42 520), aromatic nitro dyes such as 4-(2'-hydroxyethyl)aminonitrotoluene, 2-amino-4,6-dinitrophenol, 2-amino-5-(2'-hydroxyethyl) aminonitrobenzene, 2-chloro-6-(ethylamino)-4-nitrophenol, 4-chloro-N-(2-hydroxyethyl)-2-nitroaniline, 5-chloro-2-hydroxy-4-nitroaniline, 2-amino-4-chloro-6-nitrophenol and 1-(2'-ureidoethyl)amino-4-nitrobenzene, azo dyes such as sodium 6-[(4'-aminophenyl)azo]-5-hydroxynaphthalene-1-sulfonate (C.I. 14 805) and disperse dyes, for example 1,4-diaminoanthraquinone and 1,4,5,8-tetraaminoanthraquinone. The colorants of the invention can contain these dye components in an amount from about 0.1 to 4 weight percent.

The couplers and developers as well as the other dye components, provided they are bases, can, of course, also be used in the form of their physiologically tolerated salts with organic or inorganic acids, for example hydrochloric acid or sulfuric acid, or—if they contain aromatic OH groups—in the form of their salts with bases, for example as alkali metal phenoxides.

Moreover, if the colorants are to be used for coloring hair, they can also contain other common cosmetic additives, for example antioxidants such as ascorbic acid, thioglycolic acid or sodium sulfite, as well as perfume oils, complexing agents, wetting agents, emulsifiers, thickeners and hair-care agents.

The colorant of the invention can be in the form of, for example, a solution, particularly an aqueous or aqueous-alcoholic solution. A particularly preferred formulation form, however, is a cream, gel or emulsion. Such a composition consists of a mixture of the dye components and the usual additives employed for such compositions.

Common additives to solutions, creams, emulsions or gels are, for example solvents such as water, lower aliphatic alcohols, for example ethanol, propanol or isopropanol, glycerol or glycols such as 1,2-propylene glycol, moreover wetting agents or emulsifiers from the classes of anionic, cationic, amphoteric or nonionic surface-active agents, for example fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty acid alkanolamides and ethoxylated fatty esters, furthermore thickeners such as the higher fatty alcohols, starch, cellulose derivatives, petrolatum, paraffin oil and fatty acids, also hair-care agents such as cationic resins, lanolin derivatives, cholesterol, pantothenic acid and betaine. The cited constituents are used in amounts commonly employed for such purposes, for example the wetting agents and emulsifiers at a concentration of about 0.5 to 30 wt. %, the thickeners in an amount from about 0.1 to 30 wt. % and the hair-care agents at a concentration from about 0.1 to 5.0 wt. %.

Depending on the composition, the colorant of the invention can be weakly acidic, neutral or alkaline. In particular, it has a pH of 6.5 to 11.5. Adjustment to a basic pH is preferably done with ammonia, but it can also be done with an organic amine, for example monoethanolamine and triethanolamine, or with an inorganic base such as sodium hydroxide and potassium hydroxide. Suitable for adjustment to an acidic pH are inorganic or organic acids, for example phosphoric acid, acetic acid, citric acid or tartaric acid.

For oxidative dyeing of hair, the afore-described colorant is mixed with an oxidant just before use, and the resulting mixture is applied to hair in an amount sufficient for the hair-dyeing treatment, in general about 60 to 200 grams, depending on the hair fullness.

Suitable oxidants for developing the hair coloration are mainly hydrogen peroxide or its products of addition to urea, melamine, sodium borate or sodium carbonate, in the form of a 3–12%, preferably 6% aqueous solution, atmospheric oxygen also being suitable. When a 6% hydrogen peroxide solution is used as oxidant, the weight ratio of hair colorant to oxidant is from 5:1 to 1:2, but preferably 1:1. Larger amounts of oxidant are used primarily at higher dye concentrations in the hair colorant or when strong bleaching of the hair is wanted at the same time. The mixture is allowed to act on the hair at 15 to 50° C. for about 10 to 45 min, preferably 30 min, after which the hair is rinsed with water and dried. Optionally, following this rinsing, the hair is washed with a shampoo and optionally post-rinsed with a weak organic acid, for example citric acid or tartaric acid. The hair is then dried.

The colorants of the invention containing a 3-(2,5-diaminophenyl)acrylamidederivative of formula (I) as developer give hair colorations of excellent color stability, particularly in terms of light fastness, wash fastness and rubbing fastness. As far as the dyeing properties are concerned, the hair colorants of the invention provide a wide range of different color shades from blond to brown, purple, violet and even blue and black, depending on the kind and composition of the dye components. These shades have unusual color intensity. The very good coloring properties of the hair colorants of the present patent application also manifest themselves in that these colorants make it possible to dye gray keratin fibers, particularly human hair, previously not damaged chemically, without any problems and with good covering power.

The following examples illustrate the object of the invention in greater detail without limiting its scope.

EXAMPLES

I. Preparation Examples

Example 1

Synthesis of 3-(2,5-diaminophenyl)acrylamide Derivatives of Formula (I) (General Method of Synthesis)

A. Synthesis of tert.butyl(2-bromo-4-tert.butoxycarbonylaminophenyl)carbamate 15.65 g (0.07 mole) of bromo-p-phenylenediamino hydrochloride and 32.7 g (0.15 mole) of ditert.butyl dicarbonate were dissolved in a mixture of 250 mL of 2N sodium hydroxide and 250 mL of trifluorotoluene and heated to 45° C. The reaction mixture was allowed to agitate for 3 days. An additional total of 30 g (0.14 mole) of ditert.butyl dicarbonate was added stepwise. The organic layer was then separated, and the aqueous phase was extracted twice with 100-mL portions of dichloromethane. The combined extracts were evaporated, and the residue was taken up with 200 mL of hexane. The precipitate was filtered off and washed with 50 mL of hexane.

This gave 18.6 g (82% of the theoretical) of tert.butyl-(2-bromo-4tert.-butoxycarbonylaminophenyl)carbamate melting at 130° C.

B. Synthesis of tert.butyl N-(4-tert.butoxycarbonylamino-2-formylphenyl)carbamate 3.3 g (0.01 mole) of tert.butyl (2-bromo-4-tert.butoxycarbonylaminophenyl)carbamate from step A was dissolved in 100 mL of anhydrous tetrahydrofuran under argon. Then, 17 mL (0.03 mole) of a 1.6-molar ether solution of methyllitrium was added stepwise. The reaction mixture was cooled to −20° C. and to it was added stepwise 7 mL (0.01 mole) of a 1.5-molar tert.butyllithium solution. At the end of the addition, the solution was allowed to agitate for an additional 30 min at −20° C. Then, 1.2 g (0.02 mole) of dimethylformamide was added, and the reaction mixture was allowed to agitate for one hour at −20° C. The reaction mixture was then slowly warmed up to room temperature, hydrolyzed with water and poured onto diethyl ether. The aqueous phase was then extracted with diethyl ether, and the organic phase was dried with magnesium sulfate. The solvent was distilled off in a rotary evaporator, and the residue was purified on silica gel with petroleum ether/ethyl acetate (9:1).

C. Synthesis of Methyl 3-(2,5-bis-tert.butoxycarbonylaminophenyl)acrylate 9.5 g (0.03 mole) of tert.butyl N-(4-tert.butoxycarbonylamino-2-formylphenyl) carbamate from step B was dissolved in 70 mL of tetrahydrofuran, and to it was added 11.9 g (0.036 mole) of methoxycarbonylmethylene triphenylphosphorane. The reaction mixture was allowed to agitate 6 hours at room temperature. It was then poured on water and extracted with ethyl acetate. The organic phase was washed with saturated aqueous NaCl solution, dried over sodium sulfate, filtered and the filtrate evaporated. Flash chromatography of the crude product on silica gel with hexane/ethyl acetate gave 10.2 g of product (87% of the theoretical).

$^{1}$H-NMR (300 MHz. CDCl$_3$): δ=7.8 (d, 1H); 7.69 (d, 1H); 7.6 (br, 1H); 7.21 (dd, 1H); 6.50 (br, 1H); 6.40 (d, 1H); 6.35 (br, 1H); 3.8 (s, —O—CH$_3$); 1.51 (s, 18H).

D. Synthesis of 3-(2,5-bis-tert.butoxycarbonylaminophenyl)acrylic acid

To a solution of 7.1 g (0.018 mole) of methyl 3-(2,5-bis-tert.butoxycarbonylaminophenyl)acrylate from step C in 500 mL of tetrahydrofuran and 300 mL of water was added 2.53 g (0.06 mole) of lithium hydroxide monohydrate at 0° C. The mixture was allowed to agitate 48 hours at room temperature with the addition of an additional 2.53 g (0.06 mole) of lithium hydroxide monohydrate after 6 and after 24 hours. The reaction mixture was then poured into a phosphate buffer solution (pH 7.0) and extracted with ethyl acetate. The organic phase was washed with saturated aqueous NaCl solution and dried over sodium sulfate. The organic phase was partly evaporated to incipient precipitation, then hexane was added to it. The precipitate was filtered off and washed with 50 mL of hexane.

This gave 5 g (73% of the theoretical) of 3-(2,5-bis-tert.butoxycarbonylaminophenyl)acrylic acid.

$^{1}$H-NMR (300 MHz, DMSO-D$_6$): δ=12.53 (br, 1H); 9.38 ((d, 1H); 8.89 (s, 1H); 7.79 (br, 1H); 7.68 (d, 1H); 7.42 (d, 1H); 7.18 (d, 1H); 6.21 (d, 1H); 1.48 (s, 9H); 1.43 (s, 9H).

E. Synthesis of 3-(2,5-diaminophenyl)acrylamides

A mixture of 0.07 g (0.185 mmole) of 3-(2,5-bis-tert-butoxycarbonylaminophenyl)acrylic acid, 0.037 g (0.24 mmole) of N-hydroxybenzotriazole hydrate and 0.043 g (0.22 mmole) of N-(3-dimethylaminopropyl)-N'-ethylcarbodiimide hydrochloride in dichloro-methane was charged to the reactor. To the mixture were then added the appropriate amine (0.22 mmole) and 0.047 g of N-ethyldiisopropylamine and the mixture was allowed to shake 12 hours at room temperature.

At the end of the reaction, the reaction mixture was poured into 10 mL of ethyl acetate, and the organic phase was extracted with sodium hydrogen carbonate and then dried with magnesium sulfate. The solvent was distilled off in a rotatory evaporator, and the residue was purified on silica gel using an appropriate eluent (for example petroleum ether/ethyl acetate or dichloromethane/methanol). The resulting product in 4 mL of ethanol was heated to 50° C. To prepare the hydrochloride, 1.5 mL of a 2.9-molar ethanolic hydrochloric acid solution was added dropwise. The precipitate was filtered off, washed twice with 1 mL portions of ethanol and then dried.

a. N-(4-Aminophenyl)-3-(2,5-diaminophenyl)acrylamide.HCl

Amine used: tert.butyl 4-aminophenylcarbamate

Mass spectrum: MH$^+$ 269 (100)

b. 3-(2,5-Diaminophenyl)-N-ethylacrylamide.HCl

Amine used: ethylamine

Mass spectrum: MH$^+$ 206 (100)

c. 3-(2,5-Diaminophenyl)-N-furan-2-ylmethylacrylamide.HCl

Amine used: furfurylamine

Mass spectrum: MH$^+$ 258 (100)

d. N-(4-Amino-2(3)-methylphenyl)-3-(2.5-diaminophenyl)acrylamide.HCl

Amine used; tert.butyl (4-amino-2-methylphenyl) carbamate and tert.butyl (4-amino-3-methylphenyl) carbamate Mass spectrum: MH$^+$ 283 (100)

e. N-Allyl-3-(2,5-diaminophenyl)acrylamide.HCl

Amine used: allylamine

Mass spectrum: MH$^+$ 218 (100)

f. 3-(2.5-Diaminophenyl)-N-propylacylamide.HCl

Amine used: propylamine

Mass spectrum: MH$^+$ 220 (100)

g. N-[4-Amino-2(3)-(2-hydroxyethyl)phenyl]-3-(2,5-diaminophenyl)acrylamide.HCl
   Amine used: tert.butyl [4-amino-2-(2-hydroxyethyl)phenyl]carbamate and tert.butyl [4-amino-3-(2-hydroxyethyl)phenyl]carbamate
   Mass spectrum: MH$^+$ 313 (100)
h. N-Cyclopropyl-3-(2,5-diaminophenyl)acrylamide.HCl
   Amine used: cyclopropylamine
   Mass spectrum: MH$^+$ 218 (68)
i. N-[5-Amino-2-(4)-(2-hydroxyethoxy)phenyl]-3-(2,5-diaminophenyl)acrylamide.HCl
   Amine used: tert.butyl [3-amino-4-(2-hydroxyethoxy)phenyl]carbamate and tert.butyl [3-amino-6-(2-hydroxyethoxy)phenyl]carbamate
   Mass spectrum: MH$^+$ 392 (100)
j. 3-(2,5-Diaminophenyl)-N-methylacrylamide.HCl
   Amine used: methylamine
   Mass spectrum: MH$^+$ 192 (80)
k. 3-(2,5-Diaminophenyl)-N-isopropylacrylamide.HCl
   Amine used: isopropylamine
   Mass spectrum: MH$^+$ 220 (100)
l. 3-(2.5-Diaminophenyl)-N-(2-hydroxy-1-methylethyl)acrylamide.HCl
   Amine used: 2-aminopropanol
   Mass spectrum: MH$^+$ 236 (100)
m. 3-(2,5-Diaminophenyl)-N-methoxy-N-methylacrylamide.HCl
   Amine used: N,O-dimethylhydroxylamine.HCl
   Mass spectrum: MH$^+$ 222 (92)
n. 3-(2,5-Diaminophenyl)-N-[2-(3H-imidazol-4-yl)ethyl]acrylamide.HCl
   Amine used: histamine
   Mass spectrum: MH$^+$ 272 (100)
o. 3-(2,5-Diaminophenyl)-1-pyrrolidin-1-ylpropenone.HCl
   Amine used: pyrrolidine
   Mass spectrum: MH$^+$ 232 (100)
p. N-[4-[bis-(2-hydroxyethyl)amino]phenyl]-3-(2,5-diaminophenyl)acrylamide.HCl
   Amine used: 4-bis-(2-hydroxyethyl)aminoaniline
   Mass spectrum: MH$^+$ 357 (100)
q. 3-(2,5-Diaminophenyl)-1-(3-hydroxypyrrolidin-1-yl)propenone.HCl
   Amine used: 3-pyrrolidinol
   Mass spectrum: MH$^+$ 248 (100)
r. N-(3–Chloro-2-hydroxy-5-nitrophenyl)-3-(2,5-diaminophenyl)acrylamide.HCl
   Amine used: 2-amino-4-nitro-6-chlorophenol
   Mass spectrum: MH$^+$ 349 (100)
s. 3-(2,5-Diaminophenyl)-N-(4-hydroxyphenyl)acrylamide.HCl
   Amine used: 4-aminophenol
   Mass spectrum: MH$^+$ 270 (100)
t. 3-(2,5-Diaminophenyl)-N-(tetrahydrofuran-2-ylmethyl)acrylamide.HCl
   Amine used: tetrahydrofurfurylamine
   Mass spectrum: MH$^+$ 262 (100)
u. 3-(2,5-Diaminophenyl)-N-(2-hydroxy-1-hydroxymethylethyl)acrylamide.HCl
   Amine used: 3-amino-1,2-propanediol
   Mass spectrum: MH$^+$ 252 (100)
v. N-(2-Aminoethyl)-3-(2,5-diaminophenyl)acrylamide.HCl
   Amine used: ethylenediamine
   Mass spectrum: MH$^+$ 221 (100)
w. 3-(2,5-Diaminophenyl)-N-(3-imidazol-1-ylpropyl)acrylamide.HCl
   Amine used: 1-(3-aminopropyl)imidazole
   Mass spectrum: MH$^+$ 286 (100)
x. 3-(2,5-Diaminophenyl)-1-(2-hydroxymethylpyrrolidin-1-yl)propenone.HCl
   Amine used: prolinol
   Mass spectrum: MH$^+$ 262 (100)
y. 3-(2,5-Diaminophenyl)-N-(2-methoxyethyl)acrylamide.HCl
   Amine used: 2-methoxyethylamine
   Mass spectrum: MH$^+$ 236 (100)
z. 3-(2.5-Diaminophenyl)-1-morpholin-4-ylpropenone.HCl
   Amine used: morpholine
   Mass spectrum: MH$^+$ 248 (62)
aa. N-[4-Amino-2-(2-hydroxyethyl)-2H-pyrazol-3-yl]-3-(2,5-diaminophenyl)acrylamide.HCl
   Amine used: 4,5-diamino-1-(2-hydroxyethyl)pyrazole
   Mass spectrum: MH$^+$ 303 (100)
ab. 3-(2.5-Diaminophenyl)-N-(1-hydroxymethylpropyl)acrylamide.HCl
   Amine used: 2-amino-1-butanol
   Mass spectrum: MH$^+$ 250 (100)
ac. 3-(2,5-Diaminophenyl)-1-(4-hydroxypiperidin-1-yl)propenone.HCl
   Amine used: 4-hydroxypiperidine
   Mass spectrum: MH$^+$ 262 (100)
ad. N-(2-Acetylaminoethyl)-3-(2.5-diaminophenyl)acrylamide.HCl
   Amine used: N-acetylethylenediamine
   Mass spectrum: MH$^+$ 263 (100)
ae. 3-(2,5-Diaminophenyl)-N-(2-morpholin-4-ylethyl)acrylamide.HCl
   Amine used: 4-(2-ethylamino)morpholine
   Mass spectrum: MH$^+$ 291 (100)
af. 3-(2,5-Diaminophenyl)-N-[3-(2-oxopyrrolidin-1-yl)propyl]acrylamide.HCl
   Amine used: 1-(3-aminopropyl)-2-pyrrolidone
   Mass spectrum: MH$^+$ 303 (100)
ag. 2-[3-(2,5-Diaminophenyl)acryloylamino]-3-methylbutyric acid.HCl
   Amine used: α-aminoisovaleric acid
   Mass spectrum: MH$^+$ 278 (88)
ah. [3-(2,5-Diaminophenyl)acryloylamino]acetic acid.HCl
   Amine used: glycine
   Mass spectrum: (MH$^+$+CH$_3$CN) 277 (100)
ai. 3-(2,5-Diaminophenyl)-N-[2-(5-nitropyridin-2-ylamino)ethyl]acrylamide.HCl
   Amine used: 2-amino-5-nitropyridine
   Mass spectrum: MH$^+$ 343 (100)
aj. 3-(2,5-Diaminophenyl)-N-[2-(4-sulfamoylphenyl)ethyl]acrylamide.HCl
   Amine used: 4-(2-aminoethyl)benzenesulfonamide
   Mass spectrum: MH$^+$ 361 (32)
ak. N-[5–Chloro-4-(2-hydroxyethylamino)-2-nitrophenyl]-3-(2,5-diaminophenyl)acrylamide.HCl
   Amine used: 5-chloro-4-(2-hydroxyethylamino)-2-nitroaniline
   Mass spectrum: MH$^+$ 392 (28)
al. 3-(2.5-Diaminophenyl)-N-pyridin-2-ylacrylamide.HCl
   Amine used: 2-aminopyridine
   Mass spectrum: MH$^+$ 255 (100)
am. N-[3-(2,5-diaminophenyl)-2-propenoyl]-L-glutamic acid trifluoroacetate
   Amine used: L-glutamic acid
   Mass spectrum: MH$^+$ 308 (100)
an. N2-[3-(2,5-diaminophenyl)-2-propenoyl]-L-glutamine trifluoroacetate
   Amine used: L-glutamine
   Mass spectrum: MH$^+$ 307 (100)

ao. 3-(2,5-Diaminophenyl)-N-(3-hydroxy-4-methylphenyl)acrylamide.HCl
  Amine used: 5-amino-2-methylphenol
  Mass spectrum: $MH^+$ 284 (100)
ap. N-(3-Aminophenyl)-3-(2,5-diaminophenyl)acrylamide.HCl
  Amine used: tert.butyl (3-aminophenyl)carbamate
  Mass spectrum: $MH^+$ 269 (100)
aq. 3-(2,5-Diaminophenyl)-N-(3-hydroxy-5-hydroxymethyl-2-methylpyridin-4-ylmethyl)acrylamide.HCl
  Amine used: 4-aminomethyl-5-hydroxymethyl-2-methyl-3-pyridinol
  Mass spectrum: $MH^+$ 329 (100)
ar. 3-(2,5-Diaminophenyl)-N-(2-hydroxy-5-nitrophenyl)acrylamide.HCl
  Amine used: 2-amino-4-nitrophenol
  Mass spectrum: $MH^+$ 315 (100)
as. 1-f3-(2.5-Diaminophenyl)acryloyl]pyrrolidine 2-carboxamide.HCl
  Amine used: prolinamide
  Mass spectrum: $MH^+$ 275 (100)
at. [3-(2,5-Diaminophenyl)-1-(3-hydroxypiperidin-1-yl)propenone.HCl
  Amine used: 3-hydroxypiperidine
  Mass spectrum: $MH^+$ 262 (100)
av. N-(1–Carbamoyl-2-hydroxyethyl)-3-(2,5-diaminophenyl)acrylamide.HCl
  Amine used: 2-amino-3-hydroxypropionamide
  Mass spectrum: $MH^+$ 265 (100)
aw. N-[3-(2.5-Diaminophenyl)-2-propenoyl]-L-aspartic acid trifluoroacetate
  Amine used: aspartic acid
  Mass spectrum: $MH^+$ 294 (100)
ax. N2-[3-(2.5-Diaminophenyl)-2-propenoyl]-L-asparagine trifluoroacetate
  Amine used: asparagine
  Mass spectrum: $MH^+$ 293 (100)
ay. N-Benzo[1.3]dioxol-5-yl-3-(2,5-diaminophenyl)acrylamide.HCl
  Amine used: benzo[1,3]dioxol-5-ylamine
  Mass spectrum: $MH^+$ 298 (100)
az. N-[3-(2,5-Diaminophenyl)-2-propenoyl]-L-leucine.HCl
  Amine used: L-leucine
  Mass spectrum: $MH^+$ 334 (100)

Examples 2 to 36

Hair Colorants

Hair colorant solutions having the following composition were prepared:

| | |
|---|---|
| 1.25 mmoles | of developer of formula (I) as per Table 1 |
| 1.25 mmoles | of coupler according to Table 1 |
| 1.0 g | of potassium oleate (8% aqueous solution) |
| 1.0 g | of ammonia (22% aqueous solution) |
| 1.0 g | of ethanol |
| 0.3 g | of ascorbic acid |
| to 100.0 g | water |

Just before use, 50 g of the foregoing coloring solution was mixed with 50 g of a 6% aqueous hydrogen peroxide solution. The mixture was then applied to bleached hair. After an exposure time of 30 min at 40° C., the hair was rinsed with water, washed with a commercial shampoo and dried. The resulting color shades are presented in Table 1.

TABLE 1

| | | Coupler | | | |
|---|---|---|---|---|---|
| Example No. | Developer of formula (I) | I. 1,3-Dihydroxybenzene | II. 1,3-Diamino-4-(2-hydroxyethoxy)benzene sulfate | III. 5-Amino-2-methylphenol | IV. 1-Naphthol |
| 2 | As per Ex. 1a | medium blond | dark-gray | purple | gray |
| 3 | As per Ex. 1b | medium blond | blue | purple | gray |
| 4 | As per Ex. 1c | medium blond | blue-gray | purple | gray |
| 5 | As per Ex. 1d | medium blond | blue-gray | purple | gray |
| 6 | As per Ex. 1e | medium blond | blue-gray | purple | gray |
| 7 | As per Ex. 1f | medium blond | blue-gray | purple | gray |
| 8 | As per Ex. 1g | medium blond | blue-gray | purple | gray |
| 9 | As per Ex. 1h | medium blond | blue-gray | purple | gray |
| 10 | As per Ex. 1i | medium blond | blue-gray | purple | gray |
| 11 | As per Ex. 1j | medium blond | blue-gray | purple | gray |
| 12 | As per Ex. 1k | medium blond | blue-gray | purple | gray |
| 13 | As per Ex. 1l | medium blond | blue-gray | purple | gray |
| 14 | As per Ex. 1m | medium blond | blue-gray | purple | gray |

TABLE 1-continued

| | | Coupler | | | |
|---|---|---|---|---|---|
| Example No. | Developer of formula (I) | I. 1,3-Di-hydroxy-benzene | II. 1,3-Diamino-4-(2-hydroxy-ethoxy)ben-zene sulfate | III. 5-Amino-2-methyl phenol | IV. 1-Naphthol |
| 15 | As per Ex. 1n | medium blond | blue-gray | purple | gray |
| 16 | As per Ex. 1o | blond | blue-gray | purple | gray |
| 17 | As per Ex. 1p | medium blond | blue-gray | purple | gray |
| 18 | As per Ex. 1q | blond | blue-gray | purple | gray |
| 19 | As per Ex. 1r | medium blond | green | brown | green |
| 20 | As per Ex. 1s | blond | brown | red-brown | medium brown |
| 21 | As per Ex. 1t | medium blond | blue-gray | purple | gray |
| 22 | As per Ex. 1u | blond | blue-gray | purple | gray |
| 23 | As per Ex. 1v | medium blond | blue-gray | purple | gray |
| 24 | As per Ex. 1w | blond | bright-blue | bright-purple | bright-gray |
| 25 | As per Ex. 1x | blond | bright-blue | bright-purple | bright-gray |
| 26 | As per Ex. 1y | blond | bright-blue | bright-purple | bright-gray |
| 27 | As per Ex. 1z | blond | bright-blue | bright-purple | bright-gray |
| 28 | As per Ex. 1aa | bright-red | dark-violet | red | violet |
| 29 | As per Ex. 1ab | blond | bright-blue | bright-purple | bright-gray |
| 30 | As per Ex. 1ac | blond | bright-blue | bright-purple | bright-gray |
| 31 | As per Ex. 1ad | bright-blond | bright-blue | bright-purple | bright-gray |
| 32 | As per Ex. 1ae | bright-blond | bright-blue | bright-purple | bright-gray |
| 33 | As per Ex. 1af | bright-blond | bright-blue | bright-purple | bright-gray |
| 34 | As per Ex. 1ag | bright-blond | bright-blue | bright-purple | bright-gray |
| 35 | As per Ex. 1ah | bright-blond | bright-blue | bright-purple | bright-gray |
| 36 | As per Ex. 1ai | bright-blond | bright-blue | bright-purple | bright-gray |

Examples 37 to 58

Hair Colorants

Hair colorant solutions of the following composition were prepared:

| | | |
|---|---|---|
| X | g | of 3-(2,5-diaminophenyl)acrylamide derivative of formula (I) (developer E1, E2, E3 as per Table 2) |
| U | g | of developer E8 to E15 as per Table 2 |
| Y | g | of coupler K12 to K33 as per Table 3 |
| 10.0 | g | of potassium oleate (8% aqueous solution) |
| 10.0 | g | of ammonia (22% aqueous solution) |
| 10.0 | g | of ethanol |
| 0.3 | g | of ascorbic acid |
| to 100.0 | g | water |

Just before use, 30 g of the foregoing coloring solution was mixed with 30 g of a 6% aqueous solution of hydrogen peroxide. The mixture was then applied to bleached hair. After an exposure time of 30 min at 40° C., the hair was rinsed with water, washed with a commercial shampoo and dried. Table 4 shows the coloring results.

Examples 59 to 64

Hair Colorants

Dye carriers in cream form and having the following composition were prepared:

| | | |
|---|---|---|
| X | g | of 3-(2,5-diaminophenyl)acrylamide derivative of formula (I) (developer E1, E2, E3 as per Table 2) |
| U | g | of developer E8 to E15 as per Table 2 |
| Y | g | of coupler K12 to K33 as per Table 3 |
| Z | g | of 6-chloro-2-ethylamino-4-nitrophenol (D2) |
| 15.0 | g | of cetyl alcohol |
| 0.3 | g | of ascorbic acid |
| 3.5 | g | of sodium lauryl alcohol diethylene glycol ether sulfate, 28% aqueous solution |
| 3.0 | g | of ammonia, 22% aqueous solution |
| 0.3 | g | of sodium sulfite, anhydrous |
| to 100 | g | water |

Just before use, 30 g of the foregoing coloring cream was mixed with 30 g of a 6% aqueous solution of hydrogen peroxide. The mixture was then applied to the hair. After an exposure time of 30 min at 40° C., the hair was rinsed with water, washed with a commercial shampoo and dried. The coloring results are presented in Table 5.

Unless otherwise indicated, all percentages in the present patent application are by weight.

TABLE 2

| | Developers |
|---|---|
| E1 | 3-(2,5-diaminophenyl)-N-ethylacrylamide.HCl |
| E2 | N-allyl-3-(2,5-diaminophenyl)acrylamide.HCl |
| E3 | N-(4-aminophenyl)-3-(2,5-diaminophenyl)-acrylamide.HCl |
| E8 | 1,4-diaminobenzene |
| E9 | 2,5-diaminophenylethanol sulfate |
| E10 | 3-methyl-4-aminophenol |
| E11 | 4-amino-2-aminomethylphenol.2HCl |
| E12 | 4-aminophenol |
| E14 | 4,5-diamino-1-(2'-hydroxyethyl)pyrazole sulfate |
| E15 | 2,5-diaminotoluene sulfate |

TABLE 3

| | Couplers |
|---|---|
| K12 | 2-amino-4-(2'-hydroxyethyl)aminoanisole sulfate |
| K13 | 1,3-diamino-4-(2'-hydroxyethoxy)benzene sulfate |
| K21 | 3-aminophenol |
| K22 | 5-amino-2-methylphenol |
| K23 | 3-amino-2-chloro-6-methylphenol |
| K25 | 1-naphthol |
| K26 | 1-acetoxy-2-methylnaphthalene |
| K31 | 1,3-dihydroxybenzene |
| K32 | 2-methyl-1,3-dihydroxybenzene |
| K33 | 1-chloro-2,4-dihydroxybenzene |

TABLE 4

Hair Colorants

| Dyes Example No. | 37 | 38 | 39 | 40 |
|---|---|---|---|---|
| E1 | 0.30 | 0.30 | 0.35 | 0.25 |
| E10 | 0.30 | | | |
| E11 | | 0.30 | | |
| E12 | | | 0.30 | |
| E14 | | | | 0.30 |
| K31 | 0.18 | | | 0.20 |
| K32 | | 0.22 | | |
| K33 | | | 0.20 | |
| K25 | 0.30 | 0.30 | | 0.30 |
| K26 | | | 0.35 | |
| Coloring results | red-brown | red-brown | red-brown | red-brown |

| Dyes Example No. | 41 | 42 | 43 | 44 | 45 | 46 |
|---|---|---|---|---|---|---|
| E1 | 0.45 | 0.30 | 0.40 | 0.30 | 0.15 | 0.20 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring results | blond | blond | blond | blond | blond | blond |

TABLE 4-continued

Hair Colorants

| Dyes Example No. | 47 | 48 | 49 | 50 | 51 | 52 |
|---|---|---|---|---|---|---|
| E2 | 0.40 | 0.30 | 0.35 | 0.20 | 0.20 | 0.20 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring results | blond | blond | blond | blond | blond | blond |

| Dyes Example No. | 53 | 54 | 55 | 56 | 57 | 58 |
|---|---|---|---|---|---|---|
| E3 | 0.50 | 0.35 | 0.40 | 0.35 | 0.30 | 0.30 |
| E8 | | | | 0.15 | | |
| E9 | | | | | 0.15 | |
| E15 | | | | | | 0.15 |
| K12 | | | 0.10 | | | |
| K13 | 0.09 | 0.09 | | | | |
| K31 | 0.20 | | | 0.15 | 0.20 | 0.10 |
| K32 | | 0.20 | | 0.10 | | 0.10 |
| K33 | | | 0.20 | | | |
| K21 | 0.05 | | | | | |
| K22 | | 0.05 | | | | |
| K23 | | | 0.05 | 0.10 | 0.10 | 0.10 |
| Coloring results | blond | blond | blond | blond | blond | blond |

TABLE 5

Hair Colorants

| Dyes Example No. | 59 | 60 | 61 | 62 | 63 | 64 |
|---|---|---|---|---|---|---|
| E1 | 0.40 | 0.50 | | 0.80 | | 0.70 |
| E2 | | | 0.40 | | 0.90 | |
| E3 | | | | | | 1.00 |
| E9 | | 0.50 | | | | |
| E15 | 0.50 | | 0.50 | | | |
| K12 | 0.10 | 0.10 | | 0.10 | 0.10 | 0.10 |
| K23 | 0.10 | 0.10 | 0.05 | 0.10 | 0.10 | 0.10 |
| K31 | 0.40 | 0.40 | 0.40 | 0.40 | 0.40 | 0.40 |
| D2 | 0.10 | 0.10 | 0.10 | 0.10 | 0.10 | 0.10 |
| Coloring results | brown | brown | brown | brown | brown | brown |

What is claimed is:

1. A 3-(2,5-Diaminophenyl)acrylamide derivative of formula (I), or a physiologically tolerated, water-soluble salt thereof,

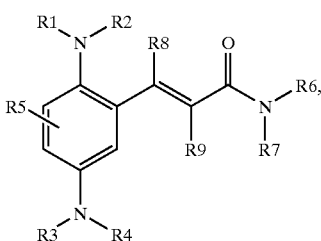

wherein R1, R2, R3 and R4 are equal or different and, independently of each other, denote hydrogen, a $C_1$–$C_6$-alkyl group, a $C_2$–$C_4$-hydroxyalkyl group or a $C_3$–$C_4$-dihydroxy alkyl group, or R1 and R2 or R3 and R4 together with N form a four-membered to eight-membered aliphatic ring and at least two of said R1, R2, R3 and R4 groups denote hydrogen;

R5 denotes hydrogen, a halogen atom, a $C_1$–$C_4$-alkyl group, a $C_1$–$C_4$-hydroxyalkyl group or a $C_1$–$C_4$-alkoxy group;

R6 and R7 are equal or different and, independently of each other, denote hydrogen, a $C_1$–$C_2$-alkoxy group, a $C_1$–$C_6$-alkyl, an unsaturated $C_3$–$C_6$-alkyl group, a $C_2$–$C_4$-hydroxyalkyl group, a $C_3$–$C_4$-dihydroxyalkyl group, a $C_2$–$C_4$-aminoalkyl group, $C_2$–$C_4$-dimethylaminoalkyl group, a $C_2$–$C_4$-acetylaminoalkyl group, a $C_2$–$C_4$-methoxyalkyl group, a $C_2$–$C_4$-ethoxyalkyl group, a $C_2$–$C_4$-cyanoalkyl group, a $C_1$–$C_4$-carboxyalkyl group, a $C_2$–$C_4$-aminocarbonylalkyl, a pyridylmethyl group, a furfuryl group, a hydrogenated furfuryl group, a substituted pyridyl group, a group of formula (II)

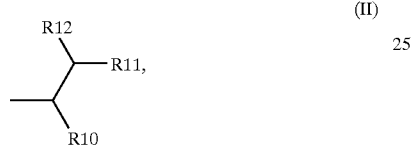

a group of formula (III)

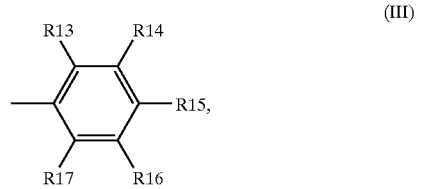

or a group of formula (IV)

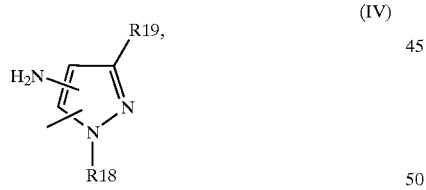

or R6 and R7 together with N form a ring of formula

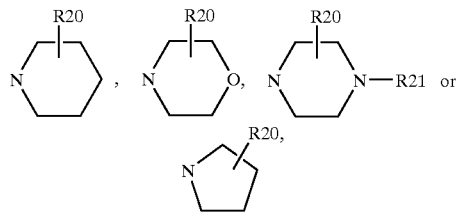

R8, R9 and R21 are equal or different and, independently of each other, denote hydrogen or a $C_1$–$C_6$-alkyl group;
R10 denotes hydrogen, a carboxy group or an aminocarbonyl group;

R11 and R12 are equal or different and, independently of each, other denote hydrogen, a hydroxyl group, an aminocarbonyl group, or methylthiomethyl group, a phenyl-substituted phenyl group, a hydroxyl-substituted phenyl group or a group of formula

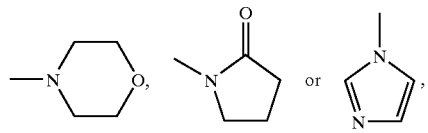

R13, R14, R15, R16 and R17 are equal or different and, independently of each other, denote hydrogen, a halogen atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkylthioether group, a mercapto group, a nitro group, an amino group, an alkylamino group, a hydroxyalkylamino group, a dialkylamino group, a di(hydroxyalkyl)amino group, a (dihydroxyalkyl)amino group, a (hydroxyalkyl)alkylamino group, a trifluoromethane group, —C(O)H, —C(O)CH$_3$, —C(O)CF$_3$, —Si(CH$_3$)$_3$, a $C_1$–$C_4$-hydroxyalkyl group, a $C_2$–$C_4$-dihydroxyalkyl group or two adjacent R13 to R17 groups together form an —O—CH$_2$—O— bridge;

R18 denotes a $C_1$–$C_4$-alkyl group, a benzyl group or a $C_1$–$C_4$-hydroxyalkyl group;

R19 denotes hydrogen or a $C_1$–$C_6$-alkyl group, and

R20 denotes hydrogen, a hydroxyl group, a carboxy group, an aminocarbonyl group or hydroxymethyl group.

2. The 3-(2,5-Diaminophenyl)acrylamide derivative as defined in claim 1, wherein one or more of said R5, R8 and R9 denote hydrogen, said R1, R2, R3 and R4 each denote hydrogen, said R6 denotes a methyl group, a methoxy group or a $C_2$–$C_4$ hydroxyalkyl group and said R7 denotes a $C_2$–$C_4$-hydroxyalkyl group, said R6 denotes hydrogen and said R7 denotes a $C_1$–$C_8$-alkyl group, an unsaturated $C_3$–$C_6$-alkyl group, a $C_2$–$C_4$-hydroxyalkyl group, a furfuryl group, a substituted phenyl group or a substituted pyrazoyl group and said R6 and R7 together with said N form an aliphatic ring of formula

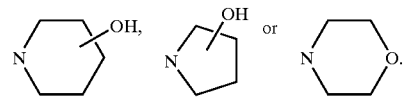

3. A 3-(2,5-Diaminophenyl)acrylamide derivative selected from the group consisting of 3-(2,5-diaminophenyl)-N-propylacrylamide, 3-(2,5-diaminophenyl)-N-furan-2-yl-methylacrylamide, 3-(2,5-diamino-phenyl)-N-methoxy-N-methylacrylamide, 3-(2,5-diaminophenyl)-N-(2-hydroxy-1-methylethyl)acrylamide, N-cyclopropyl-3-(2,5-diaminophenyl)acrylamide, 3-(2,5-diaminophenyl)-N-isopropylacrylamide, N-(4-aminophenyl)-3-(2,5-diaminophenyl)acrylamide, 3-(2,5-diaminophenyl)-1-pyrrolidin-1-yl-propenone, N-[4-amino-2-(2-hydroxyethyl)-2H-pyrazol-3-yl]-3-(2,5-diaminophenyl)acrylamide, N-(4-amino-2(3)-methylphenyl)-3-(2,5-diaminophenyl)acrylamide, N-{4-[bis-(2-hydroxyethyl)-amino]phenyl}-3-(2,5-diaminophenyl)acrylamide, 3-(2,5-diaminophenyl)-N-(4-hydroxyphenyl)acrylamide, 3-(2,5-diaminophenyl)-1-(3-hydroxypyrrolidin-1-yl)propenone, N-[5-amino-2(4)-(2- hydroxy-ethoxy)phenyl]-3-(2,5-diaminophenyl)acrylamide and 3-(2,5-diaminophenyl)-N-ethylacrylamide.

4. An agent for oxidative dyeing of keratin fibers based on a developer-coupler combination, comprising at least one coupler compound and at least one developer compound, wherein said at least one developer compound is a 3-(2,5-diaminophenyl)acrylamide derivative of formula (I), or a physiologically compatible water-soluble salt thereof:

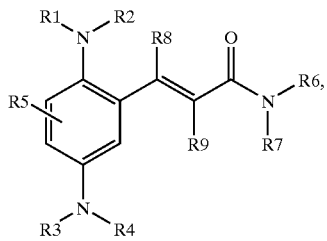
(I)

wherein R1, R2, R3 and R4 are equal or different and, independently of each other, denote hydrogen, a $C_1$–$C_6$-alkyl group, a $C_2$–$C_4$-hydroxyalkyl group or a $C_3$–$C_4$-dihydroxy alkyl group, or R1 and R2 or R3 and R4 together with N form a four-membered to eight-membered aliphatic ring and at least two of said R1, R2, R3 and R4 denote hydrogen;

R5 denotes hydrogen, a halogen atom, a $C_1$–$C_4$-alkyl group, a $C_1$–$C_4$-hydroxyalkyl group or a $C_1$–$C_4$-alkoxy group;

R6 and R7 are equal or different and, independently of each other, denote hydrogen, a $C_1$–$C_2$-alkoxy group, a $C_1$–$C_6$-alkyl group, an unsaturated $C_3$–$C_6$-alkyl group, a $C_2$–$C_4$-hydroxyalkyl group, a $C_3$–$C_4$-dihydroxyalkyl group, a $C_2$–$C_4$-aminoalkyl group, a $C_2$–$C_4$-dimethylaminoalkyl group, a $C_2$–$C_4$-acetylaminoalkyl group, a $C_2$–$C_4$-methoxyalkyl group, a $C_2$–$C_4$-ethoxyalkyl group, a $C_1$–$C_4$-cyanoalkyl group, a $C_1$–$C_4$-carboxyalkyl group, a $C_2$–$C_4$-aminocarbonylalkyl, a pyridylmethyl group, a furfuryl group, a hydrogenated furfuryl group, a substituted pyridyl group, a group of formula (II)

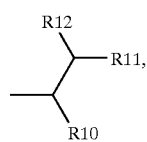
(II)

a group of formula (III)

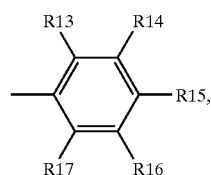
(III)

or a group of formula (IV)

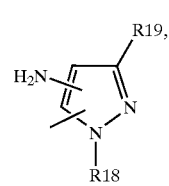
(IV)

or R6 and R7 together with N form a ring of formula

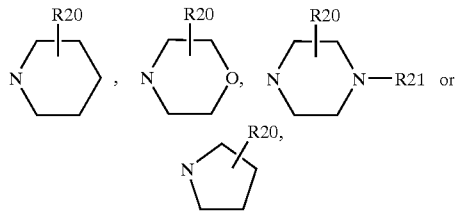

R8, R9 and R21 are equal or different and, independently of each other, denote hydrogen or a $C_1$–$C_6$-alkyl group;

R10 denotes hydrogen, a carboxy group or an aminocarbonyl group;

R11 and R12 are equal or different and, independently of each, other denote hydrogen, a hydroxyl group, an aminocarbonyl group, or methylthiomethyl group, a phenyl-substituted phenyl group, a hydroxyl-substituted phenyl group or a group of formula

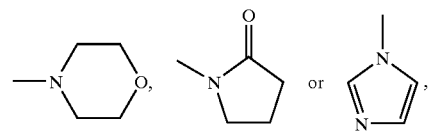

R13, R14, R15, R16 and R17 are equal or different and, independently of each other, denote hydrogen, a halogen atom, a cyano group, a hydroxyl group, a $C_1$–$C_4$-alkoxy group, a $C_1$–$C_4$-hydroxyalkoxy group, a $C_1$–$C_6$-alkyl group, a $C_1$–$C_4$-alkylthioether group, a mercapto group, a nitro group, an amino group, an alkylamino group, a hydroxyalkylamino group, a dialkylamino group, a di(hydroxyalkyl)amino group, a (dihydroxyalkyl)amino group, a (hydroxyalkyl) alkylamino group, a trifluoromethane group, —C(O)H, —C(O)CH$_3$, —C(O)CF$_3$, —Si(CH$_3$)$_3$, a $C_1$–$C_4$-hydroxyalkyl group, a $C_2$–$C_4$-dihydroxyalkyl group or two adjacent R13 to R17 groups together form an —O—CH$_2$—O— bridge;

R18 denotes a $C_1$–$C_4$-alkyl group, a benzyl group or a $C_1$–$C_4$-hydroxyalkyl group;

R19 denotes hydrogen or a $C_1$–$C_6$-alkyl group, and

R20 denotes hydrogen, a hydroxyl group, a carboxy group, an aminocarbonyl group or a hydroxymethyl group.

5. The agent as defined in claim 4, containing the 3-(2, 5-diaminophenyl)acrylamide derivative of formula (I) in an amount from 0.005 to 20 weight percent.

6. The agent as defined in claim 4, wherein said at least one coupler compound is selected from the group consisting of N-(3-dimethyl-aminophenyl)urea, 2,6-diaminopyridine, 2-amino-4-[(2-hydroxyethyl)-amino]-anisole, 2,4-diamino- 1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)-benzene, 1,3-diamino-4-(2,3-dihydroxy-propoxy)benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diamino-phenoxyacetic acid, 3-[di(2-hydroxyethyl)-amino]aniline, 4-amino-2-di[(2-hydroxy-ethyl)-amino]-1-ethoxybenzene, 5-methyl-2-(1-methylethyl)phenol, 3-[(2-hydroxy-ethyl)amino]-aniline, 3-[(2-aminoethyl)-amino]aniline, 1,3-di(2,4-diaminophenoxy)-propane, di(2,4-diaminophenoxy)-methane, 1,3-diamino-2,4-dimethoxybenzene, 2,6-bis(2-hydroxyethyl)aminotoluene, 4-hydroxyindole, 3-dimethylaminophenol, 3-diethylaminophenol, 5-amino-2-methylphenol, 5-amino-4-fluoro-2-methyl-phenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methyl-phenol, 3-amino-2-chloro-6-methylphenol, 3-aminophenol, 2-[(3-hydroxyphenyl)-amino]acetamide, 5-[(2-hydroxyethyl)amino]-4-methoxy-2-methylphenol, 5-[(2-hydroxyethyl)-amino]-2-methylphenol, 3-[(2-hydroxy-ethyl)amino]phenol, 3-[(2-methoxyethyl)-amino]phenol, 5-amino-2-ethylphenol, 5-amino-2-methoxyphenol, 2-(4-amino-2-hydroxyphenoxy)-ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)-amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole, 2,3-indolinedione, 1,3-diamino-4-(3-hydroxypropoxy)benzene, 1,3-diamino-4-(2-methoxyethoxy)benzene and 2,6-dihdroxy-3,4-dimethylpyridine.

7. The agent as defined in claim 4, further comprising, in addition to the 3-(2,5-diaminophenyl)acrylamide derivative of formula (I), or the salt thereof, at least one other developer compound selected from the group consisting of 1,4-diaminobenzene, 2,5-diaminotoluene, 1-(2,5-diaminophenyl)ethanol, 2-(2,5-diaminophenyl)ethanol, 4-aminophenol, 4,5-diaminopyrazole derivatives and tetraaminopyrimidines.

8. The agent as defined in claim 4, wherein said at least one developer compound and said at least one coupler compound are present in a total amount from 0.005 to 20 weight percent.

9. The agent as defined in claim 4, further comprising at least one direct dye.

10. The agent as defined in claim 4, having a pH of 6.5 to 11.5.

11. The agent as defined in claim 4, consisting of a hair colorant.

* * * * *